United States Patent
Zhang et al.

(10) Patent No.: US 12,209,966 B1
(45) Date of Patent: Jan. 28, 2025

(54) TEST DEVICE AND TEST METHOD FOR ISOTOPE MEASUREMENT OF NOBLE GASES IN LUNAR SOIL

(71) Applicant: Institute of Geology and Geophysics, Chinese Academy of Sciences, Beijing (CN)

(72) Inventors: Xuhang Zhang, Beijing (CN); Fei Su, Beijing (CN); Huaiyu He, Beijing (CN)

(73) Assignee: Institute of Geology and Geophysics, Chinese Academy of Sciences, Beijing (CN)

( * ) Notice: Subject to any disclaimer, the term of this patent is extended or adjusted under 35 U.S.C. 154(b) by 0 days.

(21) Appl. No.: 18/829,304

(22) Filed: Sep. 10, 2024

(30) Foreign Application Priority Data

May 30, 2024 (CN) .......................... 202410685694.0

(51) Int. Cl.
| | | |
|---|---|---|
| *G01N 21/74* | (2006.01) | |
| *G01N 1/40* | (2006.01) | |
| *H01J 49/00* | (2006.01) | |
| *H01J 49/04* | (2006.01) | |
| *G01N 33/00* | (2006.01) | |

(52) U.S. Cl.
CPC .............. *G01N 21/74* (2013.01); *G01N 1/405* (2013.01); *H01J 49/0031* (2013.01); *H01J 49/0422* (2013.01); *H01J 49/0468* (2013.01); *G01N 33/0013* (2013.01); *G01N 33/0036* (2013.01)

(58) Field of Classification Search
CPC .... G01N 21/74; G01N 1/405; G01N 33/0013; G01N 33/0036; H01J 49/0031; H01J 49/0422; H01J 49/0468
USPC .......................................... 250/281, 282, 288
See application file for complete search history.

(56) References Cited

U.S. PATENT DOCUMENTS

2016/0061798 A1\* 3/2016 Wapelhorst ........ G01N 33/0011
356/402

\* cited by examiner

*Primary Examiner* — Michael Maskell

(57) ABSTRACT

The disclosure provides a test device and a test method for isotope measurement of noble gases in lunar soil. The testing device includes a carbon dioxide laser ultra-high vacuum sample melting system, zirconium-aluminum getters, a vacuum dry pump, a first molecular pump, a second molecular pump, a neon gas capture unit, an argon gas capture unit, an argon krypton-xenon capture unit, a dilution tank, a sputtering ion pump and a noble gas mass spectrometer which are connected through pipelines, and each pipeline and each component are connected through a specific way; in addition, control valves for controlling the opening and closing of the pipelines are installed on the connection path between each pipeline and each component, and the disclosure also provides a matching test method.

10 Claims, 1 Drawing Sheet

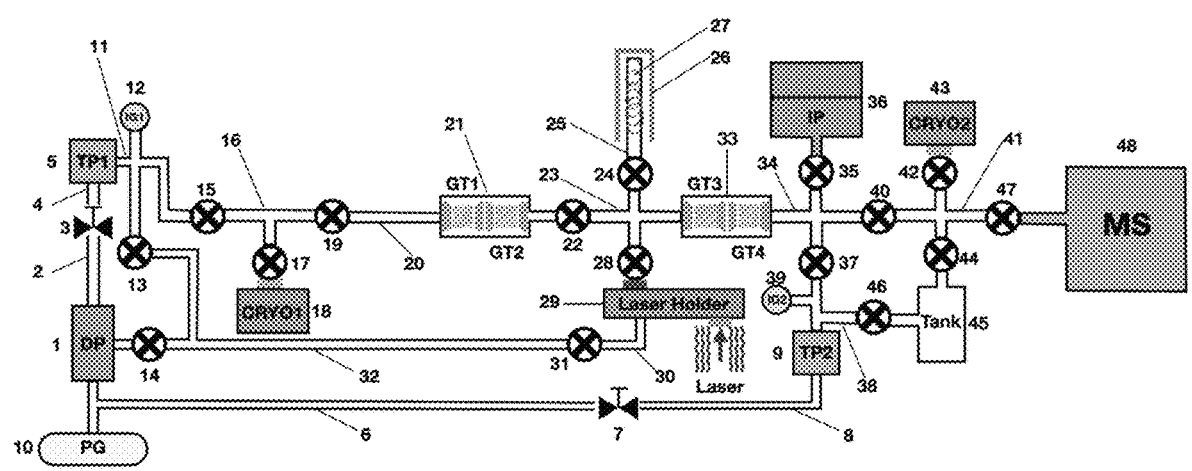

TEST DEVICE AND TEST METHOD FOR ISOTOPE MEASUREMENT OF NOBLE GASES IN LUNAR SOIL

TECHNICAL FIELD

The disclosure relates to a technical field of isotope measurement of noble gases in lunar soil, and in particular to a test device and a test method for isotope measurement of noble gases in lunar soil.

BACKGROUND

With the return of Chang'e-5 lunar samples, a series of lunar soil samples analysis methods have been established, marking the vigorous development of planetary science in China. It has been found by predecessors that lunar soil samples are significantly different with meteorite and earth samples in terms of isotopes, especially in the abundance of noble gases. For example, helium, a noble gas element, is 6 orders of magnitude more abundant in lunar soil than in Earth's atmosphere. Similarly, the abundance and the composition of neon, argon, krypton and xenon in lunar soil are also pretty different from that in the earth's atmosphere. This makes the original method for measuring noble gases in earth samples is not appropriate for studying lunar soil. Normally, the concentration of helium in lunar soil samples is nine orders of magnitude higher than that of xenon, so when the xenon isotope in lunar soil samples satisfies the analysis conditions of the electron multiplier of the noble gas mass spectrometer, the helium concentration has obviously exceeded the measurable range of noble gas mass spectrometer. However, the concentration of helium in the earth atmosphere is only 58 times higher than that of xenon. When xenon isotope satisfies the analysis conditions of the noble gas mass spectrometer, Faraday cup can still be used to measure helium in the earth atmosphere.

Noble gases in lunar soils not only represent a potential new energy resource but also encapsulate critical information regarding the evolution of the solar system. Currently, there is no established method in China for the analysis of noble gases (helium, neon, argon, krypton, and xenon) in lunar soil that can both minimize the usage of lunar soil samples and meet the stringent requirements for high-precision measurement and analysis. This lack of an appropriate testing method has significantly impeded research on noble gases in lunar soil within China.

SUMMARY

In view of the shortcomings mentioned in the prior art, a test device and a test method for isotope measurement of noble gases in lunar soil are provided by the present disclosure. The present disclosure provides a test device and a test method for obtaining isotope and abundance information of helium, neon, argon, krypton, and xenon from a lunar soil sample. Specifically, the noble gases can be separated by controlling the valve, the cold pump, and the dilution tank in unison, thereby markedly reducing the quantity of lunar soil samples necessary to obtain isotope and abundance data for helium, neon, argon, krypton, and xenon, and enhancing the efficacy of analysis and testing.

The present disclosure is obtained through the following technical scheme with the aim of achieving the above-mentioned objects and other related objects.

The disclosure provides a test device and a test method for isotope measurement of noble gases in lunar soil, including a carbon dioxide laser ultra-high vacuum sample melting system, a first zirconium-aluminum getter, a second zirconium-aluminum getter, a vacuum dry pump, a first molecular pump, a second molecular pump, a neon gas capture unit, an argon gas capture unit, an argon-krypton-xenon capture unit, a dilution tank, a sputtering ion pump and a noble gas mass spectrometer which are connected through pipelines;

the pipelines include a first CF cross, a first CF tee, a first CF two-way, a second CF cross, a second CF two-way, a second CF tee, a third CF cross, a fourth CF cross and a fifth CF cross, where four ports of the first CF cross are respectively connected with the first molecular pump, the second CF tee, the first CF tee and a pressure detection unit; the remaining two ports of the second CF tee are respectively connected with the second CF two-way and the vacuum dry pump; the other port of the second CF two-way is connected with the carbon dioxide laser ultra-high vacuum sample melting system; the remaining two ports of the first CF tee are respectively connected with the neon gas capture unit and the first zirconium-aluminum getter through the first CF two-way; the four ports of the second CF cross are respectively connected with the first zirconium-aluminum getter, the argon gas capture unit, the second zirconium-aluminum getter and the carbon dioxide laser ultra-high vacuum sample melting system; the four ports of the third CF cross are respectively connected with the second zirconium-aluminum getter, the sputtering ion pump, the fourth CF cross and the fifth CF cross; the remaining three ports of the fourth CF cross are respectively connected with the pressure detection unit, the dilution tank and the second molecular pump; the remaining three ports of the fifth CF cross are respectively connected with the argon-krypton-xenon capture unit, the dilution tank and the noble gas mass spectrometer;

and control valves for controlling the opening and closing of the pipelines are installed on the connection path between each pipeline and each component.

In various practical examples, the control valves are all pneumatic valves.

In various practical examples, the second CF tee connects to the first CF cross via a first pneumatic valve and to the vacuum dry pump via a second pneumatic valve; the first CF tee connects to the first CF cross via a third pneumatic valve, to the neon gas capture unit via a fourth pneumatic valve and to the first CF two-way via a fifth pneumatic valve; the second CF cross connects to the first zirconium-aluminum getter via a sixth pneumatic valve, to the argon gas capture unit via a seventh pneumatic valve and to the carbon dioxide laser ultra-high vacuum sample melting system via an eighth pneumatic valve; the second CF two-way connects to the second CF tee via a ninth pneumatic valve; the third CF cross connects to the sputtering ion pump via a tenth pneumatic valve, to the fourth CF cross via an eleventh pneumatic valve and to the fifth CF cross via a twelfth pneumatic valve; the fifth CF cross connects to the argon-krypton-xenon capture unit via a thirteenth pneumatic valve, to the dilution tank via a fourteenth pneumatic valve and to the noble gas mass spectrometer via a sixteenth pneumatic valve.

In various practical examples, the neon gas capture unit is a cryopump containing activated carbon; and/or the argon-krypton-xenon capture unit is a cryopump without activated carbon.

In various practical examples, an oxygen-free copper gasket is positioned at the sample cavity entrance of the carbon dioxide laser ultra-high vacuum sample melting system, ensuring a hermetic seal of the cavity.

In various practical examples, the argon gas capture unit includes an activated carbon-containing cold trap, a liquid nitrogen bracket and a temperature-controlled heating wire, where the activated carbon-containing cold trap is arranged in the liquid nitrogen bracket, the temperature-controlled heating wire is arranged outside the activated carbon-containing cold trap, and the activated carbon-containing cold trap is communicated with the second CF cross.

In various practical examples, the device also includes a first bellows, a second bellows, a third bellows, a first isolation valve, a KF tee and a second isolation valve; the first molecular pump is sequentially connected with the second bellows, the first isolation valve and the first bellows, and then connected with the vacuum dry pump; the second molecular pump is sequentially connected with the third bellows, the second isolation valve and the KF tee, and then connected with the pressure detection unit and the vacuum dry pump respectively; the remaining port of the KF tee is connected with the pressure detection unit.

In various practical examples, the pressure detection unit is a resistance gauge or an ionization gauge; and/or the first zirconium-aluminum getter and the second zirconium-aluminum getter respectively include at least one zirconium-aluminum pump; and/or volumes of the pipelines and components of the test device are specified as known constants.

A test method for isotope measurement of noble gases in lunar soil is provided in the second aspect of the disclosure, and the test device provided in the first aspect is applied in the test method, the test method includes the following steps:

1) loading of the lunar soil sample:
   keeping the test device under vacuum conditions except the carbon dioxide laser ultra-high vacuum sample melting system by manipulating the control valve, and loading the lunar soil sample into the cavity of the carbon dioxide laser ultra-high vacuum sample melting system.

2) Removal of adsorbed gas from the lunar soil sample surface:
2-1) only maintaining the carbon dioxide laser ultra-high vacuum sample melting system, the second CF two-way and the second CF tee in conjunction with the vacuum dry pump to establish a conduction transport pathway by manipulating the control valve, so as to carry out the first pumping on the carbon dioxide laser ultra-high vacuum sample melting system by the vacuum dry pump;
2-2) baking the lunar soil sample at a baking temperature of 110° C.-130° C.; only maintaining the carbon dioxide laser ultra-high vacuum sample melting system, the second CF two-way, and the second CF tee in conjunction with the first molecular pump to establish a conduction transport pathway by manipulating the control valve, so as to carry out the second pumping on the carbon dioxide laser ultra-high vacuum sample melting system by the first molecular pump; and
2-3) terminating the baking process, and then baking the lunar soil sample when the lunar soil sample is cooled to room temperature (the room temperature is 20° C.-25° C.); only maintaining the carbon dioxide laser ultra-high vacuum sample melting system, the second zirconium-aluminum getter and the third CF cross in conjunction with the sputtering ion pump to establish a conduction transport pathway by manipulating the control valve, so as to carry out the third pumping on the carbon dioxide laser ultra-high vacuum sample melting system by the sputtering ion pump.

3) Extraction and purification:
3-1) heating the lunar soil sample through the diamond window by the carbon oxide laser for gas extraction to obtain extracted lunar soil gas; and
3-2) only maintaining the first zirconium-aluminum getter and the second zirconium-aluminum getter in conjunction with the carbon dioxide laser ultra-high vacuum sample melting system to establish a conduction transport pathway by manipulating the control valve, enabling the first zirconium-aluminum getter and the second zirconium-aluminum getter to purify the extracted lunar soil gas, remove active gas in the extracted gas and leave only extracted noble gas.

4) Diffusion of noble gas:
4-1) diffusing the noble gas extracted from lunar soil by manipulating the control valve to an enclosed diffusion area, the enclosed diffusion area is formed by the first CF tee, the first CF two-way, the first zirconium-aluminum getter, the second CF cross, the third CF cross, the fifth CF cross and the dilution tank; and
4-2) dispersing the noble gas in the enclosed diffusion area into a first enclosed diffusion area and a second enclosed diffusion area by manipulating the control valve between the first CF tee and the first CF two-way, where the first enclosed diffusion area is in the first CF tee (16) and the second enclosed diffusion area is the enclosed diffusion area except the first enclosed diffusion area.

5) Gas capture:
5-1) by manipulating the control valve and by closing the control valve between the first CF tee and the first CF two-way, only maintaining the first CF two-way, the first zirconium-aluminum getter, the second CF cross, the third CF cross, the fifth CF cross, and the dilution tank in conjunction with the argon-krypton-xenon capture unit to establish a conduction transport pathway, capturing argon, krypton and xenon gases in the noble gases in the second enclosed diffusion area by the argon-krypton-xenon capture unit to obtain argon-krypton-xenon gas; and carrying out the fourth pumping on the helium gas and neon gas not being captured in the pipelines by the second molecular pump by manipulating the control valve after capture;
5-2) by opening the control valve between the first CF tee and the first CF two-way, only maintaining the argon gas capture unit communicating with the noble gases in the first enclosed diffusion area, enabling the argon gas capture unit to capture argon gas in the noble gases; and
5-3) only maintaining the neon gas capture unit communicating with the noble gases in the first enclosed diffusion area by manipulating the control valve, enabling the neon gas capture unit to capture the neon gas in the first enclosed diffusion area.

6) Gas measurement:
the specific measurement steps of helium-neon-argon for the first time are as follows:
6-1) only enabling helium gas in the fifth CF cross in the enclosed area into the noble gas mass spectrometer by manipulating the control valve for measurement, and pumping the remaining helium gas in the pipelines by the first molecular pump to remove the helium gas in the pipelines after measurement;
6-2) releasing the neon gas in the neon gas capture unit into the pipelines by manipulating the control valve, enabling the neon gas to enter the noble gas mass spectrometer, and pumping the remaining neon gas in the pipelines by the first molecular pump to remove the neon gas in the pipelines after measurement;

6-3) releasing the argon gas in the argon gas capture unit into the pipelines by manipulating the control valve, opening the sixteenth pneumatic valve after release to make the argon enter the noble gas mass spectrometer, and pumping the remaining argon gas in the pipelines by the first molecular pump to remove the argon gas in the pipelines after measurement;

the specific measurement steps of argon (for the second time), krypton and xenon are as follows:

6-4) where the argon-krypton-xenon capture unit is a cryopump without activated carbon; setting the cryopump without activated carbon at a temperature of 78-82 Kelvin (K), and releasing the argon into the pipelines of the third enclosed diffusion area, where the third enclosed diffusion area includes the fifth CF cross and the cryopump without activated carbon; opening the sixteenth pneumatic valve to make the argon gas enter the noble gas mass spectrometer, and pumping the remaining argon gas in the pipelines by the first molecular pump to remove the argon gas in the pipelines after measurement;

6-5) setting the cryopump without activated carbon at a temperature of 101-105 K, releasing krypton gas into the pipelines of the third enclosed diffusion area to make the krypton gas enter the noble gas mass spectrometer, and pumping the remaining krypton gas in the pipelines by the first molecular pump to remove the krypton gas in the pipelines after measurement; and 6-6) setting the cryopump without activated carbon at a temperature of 152-157 K, releasing xenon gas into the pipelines of the third enclosed diffusion area to make the xenon gas enter the noble gas mass spectrometer; and pumping the remaining xenon gas in the pipelines by the first molecular pump to remove the xenon gas in the pipelines after measurement.

In various practical examples, the first isolation valve and the second isolation valve are closed during the first pumping.

In various practical examples, the first pumping is at an end point of 0.1-10 Pa; and/or the second pumping is at an end point of $0.5-2*10^{-5}$ Pa.

In various practical examples, the third pumping is at an end point of $(0.5-2)*10^{-8}$ Pa; and/or, the fourth pumping is at an end point of $0.5-2*10^{-7}$ Pa and/or the fifth pumping is at an end point of $0.5-2*10^{-7}$ Pa.

V1-V6 are all known constants.

Specifically, the volume of the enclosed diffusion area is V1, the volume of the first enclosed diffusion area is V2, the volume of the second enclosed diffusion area is V3, the volume of the argon-krypton-xenon capture unit is V4, the volume of the fifth CF cross is V5, the volume of the noble gas mass spectrometer is VMS, and the volume of the third enclosed diffusion area is V6.

The test device, provided in the first aspect of the disclosure, in conjunction with specific testing methods, is capable of conducting high-precision measurements of the isotopes and abundances for helium, neon, argon, krypton, and xenon present within lunar soil. The disclosure enables the comparison of all noble gas isotope systems within a single sample.

In the test method provided by the disclosure, multiple gas diffusion is involved, and in order to finally obtain the absolute concentration of each noble gas in the lunar soil sample, it is only necessary to know the gas intake ratio of helium-neon-argon (the first time)-argon (the second time)-krypton-xenon measured in the noble gas mass spectrometer in the step 6) to finally calculate a concentration of the purified initial noble gas released from the lunar soil.

Particularly, in the test method provided by the disclosure, two gas measurements of argon (the first time) and argon (the second time) are involved in the step 6), thus effectively calibrating the concentration of each noble gas in this method. The measurement of argon (the first time) and the measurement of argon (the second time) involve the capture and release of different gas proportions in the same lunar soil. The specific volumes of components involved in each enclosed area in the method are known. The inverse calculated final amount of initial argon from the measurement results of argon (the first time) and argon (the second time) combined with the intake ratio should be consistent and can be used to represent the gas concentration of argon in the lunar soil. Specifically, the inverse calculated final amount of initial argon (the second time) ($n_2Ar$; $n_2Ar=a_2Ar/b_2\%$) from the measurement result ($a_2Ar$) of argon (the second time) combined with the intake ratio ($b_2\%$) can better represent the amount of argon gas in lunar soil. b2% is obtained according to the ideal gas state equation PV=nRT and the purification system volume, $b2\%=V5*V3/V6/(VMS+V5)*VMS/V1*100$. Similarly, the intake ratio of argon (the first time) is $b1\%=V5*V2/V6/(VMS+V5)*VMS/V1*100$. Because it mainly comes from the capture of argon in the dilution tank in the step 5), it accounts for a higher proportion of argon in the initial gas, experiences less areas with components, and may cause less errors. If it is observed that there is a certain difference between the initial argon (the first time) amount ($n_1Ar$) corresponding to argon (the first time) and $n_2Ar$, a calibration factor a of $n_1Ar/n_2Ar=a$ is obtained. Based on this, the initial helium (nHe) and Neon (nNe) in the lunar soil by $a*nM(M=He, Ne)$ are calculated. The initial krypton and xenon in lunar soil are consistent with the elements experienced in the capture and release steps 5) and 6) of argon (the second time), so the calibration step is unnecessary.

To sum up, the disclosure has at least the following beneficial effects:

According to the test device, the isotopes and abundances of helium, neon, argon, krypton and xenon within milligram quantities of lunar soil are measurable with exceptional precision. The disclosure minimizes the quantity of lunar soil required for testing, enhance experimental efficiency and ensures comparison of noble gas isotope systems in the same sample.

BRIEF DESCRIPTION OF THE DRAWING

FIG. 1 is a schematic structural diagram of a test device for isotope measurement of noble gases in lunar soil provided by the present disclosure.

In the FIGURE:

1. vacuum dry pump; 2. first bellows; 3. first isolation valve; 4. second bellows; 5. first molecular pump; 6. KF tee; 7. second isolation valve; 8. third bellows; 9. second molecular pump; 10. resistance gauge; 11. first CF cross; 12. first ionization gauge; 13. first pneumatic valve; 14. second pneumatic valve; 15. third pneumatic valve; 16. first CF tee; 17. fourth pneumatic valve; 18. cryopump containing activated carbon; 19. fifth pneumatic valve; 20. first CF two-way; 21. first zirconium-aluminum getter; 22. sixth pneumatic valve; 23. second CF cross; 24. seventh pneumatic valve; 25. activated carbon-containing cold trap; 26. liquid nitrogen bracket; 27. temperature-controlled heating wire; 28. eighth pneumatic valve; 29. carbon dioxide laser ultra-high vacuum sample melting system; 30. second CF two-way; 31. ninth pneumatic valve; 32. second CF tee; 33. second zirconium-aluminum getter; 34. third CF cross; 35. tenth pneumatic valve; 36. sputtering ion pump; 37. eleventh pneumatic valve; 38. fourth CF cross; 39. second ionization gauge; 40. twelfth pneumatic valve; 41. fifth CF cross; 42. thirteenth pneumatic valve; 43. cryopump without activated carbon; 44. fourteenth pneumatic valve; 45. dilution tank; 46. fifteenth pneumatic valve; 47. sixteenth pneumatic valve; and 48. noble gas mass spectrometer.

DETAILED DESCRIPTION OF THE EMBODIMENTS

Because there is a great difference between the abundance of noble gas in lunar soil and the abundance of earth samples, it is easy to have the problem that the helium isotope obviously exceeds the Faraday cup limit when xenon isotope meets the measurement requirements of electron multiplier during the measurement by the noble gas mass spectrometer. Lunar soil is extremely precious, so it is necessary to measure and analyze isotopes of all noble gases in lunar soil under the condition of consuming the same sample amount. The disclosure is suitable for separating and diluting noble gases in lunar soil by controlling a purification system, so as to meet the test conditions of the noble gas mass spectrometer. Moreover, the initial concentrations of helium, neon, argon, krypton and xenon in lunar soil can be better calibrated by measuring argon twice, which eliminates some potential interference of diffusion ratio conversion.

The implementation of the present disclosure is described by specific embodiments, and people familiar with this technology can easily understand other advantages and effects of the present disclosure from the contents disclosed in this specification. Before further describing the specific embodiments of the present disclosure, it should be understood that the scope of protection of the present disclosure is not limited to the following specific embodiments; it should also be understood that the terminology used in the embodiments of the present disclosure is for the purpose of describing specific embodiments, and not for the purpose of limiting the protection scope of the present disclosure. The test methods for which specific conditions are not specified in the following examples are usually in accordance with conventional conditions or those suggested by various manufacturers.

When the embodiments give numerical ranges, it should be understood that unless otherwise specified in the present disclosure, two endpoints of each numerical range and any numerical value between the two endpoints can be selected. Unless otherwise defined, all technical and scientific terms used in the present disclosure have the same meaning as commonly understood by those skilled in the art. In addition to the specific methods, equipment and materials used in the embodiment, according to the mastery of the prior art by the technicians in the technical field and the records of the present disclosure, any method, equipment and materials in the prior art similar to or equivalent to the methods, equipment and materials described in the embodiment of the present disclosure can be used to realize the present disclosure.

Embodiment 1

Referring to FIG. 1, a test device and a test method for isotope measurement of noble gases in lunar soil includes a carbon dioxide laser ultra-high vacuum sample melting system 29, a first zirconium-aluminum getter 21, a second zirconium-aluminum getter 33, a vacuum dry pump 1, a first molecular pump 5, a second molecular pump 9, a neon gas capture unit, an argon gas capture unit, an argon-krypton-xenon capture unit, a dilution tank 45, a sputtering ion pump 36 and a noble gas mass spectrometer 48 which are connected through pipelines. The pipelines include a first CF cross 11, a first CF tee 16, a first CF two-way 20, a second CF cross 23, a second CF two-way 30, a second CF tee 32, a third CF cross 34, a fourth CF cross 38 and a fifth CF cross 41, where four ports of the first CF cross 11 are respectively connected with the first molecular pump 5, the second CF tee 32, the first CF tee 16 and the first ionization gauge 12; the remaining two ports of the second CF tee 32 are respectively connected with the second CF two-way 30 and the vacuum dry pump 1; the other port of the second CF two-way 30 is connected with the carbon dioxide laser ultra-high vacuum sample melting system 29; the remaining two ports of the first CF tee 16 are respectively connected with the neon gas capture unit and the first zirconium-aluminum getter 21 through the first CF two-way 20; the four ports of the second CF cross 23 are respectively connected with the first zirconium-aluminum getter 21, the argon gas capture unit, the second zirconium-aluminum getter 33 and the carbon dioxide laser ultra-high vacuum sample melting system 29; the four ports of the third CF cross 34 are respectively connected with the second zirconium-aluminum getter 33, the sputtering ion pump 36, the fourth CF cross 38 and the fifth CF cross 41; the remaining three ports of the fourth CF cross 38 are respectively connected with a second ionization gauge 39, the dilution tank 45 and the second molecular pump 9; the remaining three ports of the fifth CF cross 41 are respectively connected with the argon-krypton-xenon capture unit, the dilution tank 45 and the noble gas mass spectrometer 48. Moreover, a control valve is provided on the communication path between each pipeline and each component to control the opening and closing of the pipeline. Specifically, the second CF tee 32 connects to the first CF cross 11 via a first pneumatic valve 13 and to the vacuum dry pump 1 via a second pneumatic valve 14; the first CF tee 16 connects to the first CF cross 11 via a third pneumatic valve 15, to the neon gas capture unit via a fourth pneumatic valve 17 and to the first CF two-way 20 via a fifth pneumatic valve 19; the second CF cross 23 connects to the first zirconium-aluminum getter 21 via a sixth pneumatic valve 22, to the argon gas capture unit via a seventh pneumatic valve 24 and to the carbon dioxide laser ultra-high vacuum sample melting system 29 via an eighth pneumatic valve 28; the second CF two-way 30 connects to the second CF tee 32 via a ninth pneumatic valve 31; the third CF cross 34 connects to the sputtering ion pump 36 via a tenth pneumatic valve 35, to the fourth CF cross 38 via an eleventh pneumatic valve 37 and to the fifth CF cross 41 via a twelfth pneumatic valve 40; the fifth CF cross 41 connects to the argon-krypton-xenon capture unit via a thirteenth pneumatic valve 42, to the dilution tank 45 via a fourteenth pneumatic valve 44 and to the noble gas mass spectrometer 48 via a sixteenth pneumatic valve 47.

Referring to FIG. 1 again, the device also includes a first bellows 2, a second bellows 4, a third bellows 8, a first isolation valve 3, a KF tee 6 and a second isolation valve 7; the first molecular pump 5 is sequentially connected with the second bellows 4, the first isolation valve 3 and the first bellows 2, and then connected with the vacuum dry pump 1; the second molecular pump 9 is sequentially connected with the third bellows 8, the second isolation valve 7 and the KF tee 6, and then connected with the pressure detection unit and the vacuum dry pump 1 respectively; the remaining port of the KF tee 6 is connected with a resistance gauge 10.

Referring to FIG. 1, the argon gas capture unit includes an activated carbon-containing cold trap 25, a liquid nitrogen bracket 26 and a temperature-controlled heating wire 27, where the activated carbon-containing cold trap 25 is arranged in the liquid nitrogen bracket 26, the temperature-controlled heating wire 27 is arranged outside the activated carbon-containing cold trap 25, and the activated carbon-containing cold trap 25 is communicated with the second CF cross 23.

In this embodiment, the control valves are all pneumatic valves, and the vacuum dry pump 1 is a dry pump. The neon gas capture unit is a cryopump 18 containing activated carbon, and the argon-krypton-xenon capture unit is a cryopump 43 without activated carbon. An oxygen-free copper gasket is arranged at the sample cavity opening of the carbon dioxide laser ultra-high vacuum sample melting system 29 to seal the sample cavity.

Embodiment 2

A test method is provided and is carried out by using the test device of Embodiment 1, specifically:

1) Loading of lunar soil: during the loading procedure, the cavity of the carbon dioxide laser ultra-high vacuum sample melting system 29 needs to be opened to load lunar soil. Before opening the cavity, the eighth pneumatic valve 28 and the ninth pneumatic valve 31 are closed, so that when the carbon dioxide laser ultra-high vacuum sample melting system 29 is exposed to the atmosphere, the rest of the purification system remains in the ultra-high vacuum state. After the lunar soil sample is loaded into the cavity of carbon dioxide laser ultra-high vacuum sample melting system 29, oxygen-free copper gasket is used to seal the cavity edge flange.

2) Removal of adsorbed gas from lunar soil samples: because both the lunar soil sample and the cavity of the carbon dioxide laser ultra-high vacuum sample melting system are exposed to the earth's atmosphere during the loading procedure, leading to a certain adsorption of atmospheric gases on the cavity surface and the lunar soil surface, and the adsorbed atmospheric gases needs to be removed. First, the second pneumatic valve 14 and the ninth pneumatic valve 31 are opened, the first pneumatic valve 13 is closed, and the carbon dioxide laser ultra-high vacuum sample melting system 29 is connected through the second CF two-way 30 and the second CF tee connection 32 of the gas conveying pipeline, so that the vacuum dry pump 1 can pump the carbon dioxide laser ultra-high vacuum sample melting system 29 from the earth's atmosphere state (101325 Pa) to the primary vacuum state (~1 Pa). In particular, it is necessary to close the first isolation valve 3 and the second isolation valve 7 during pumping, so as to prevent the situation affecting the working state of the molecular pumps that the high pressure difference during pumping diffuses gas back to the first molecular pump 5 and the second molecular pump 9. When the reading of resistance gauge 10 is 1 Pa, the pumping is over. At this time, the first isolation valve 3 and the second isolation valve 7 are opened, the second pneumatic valve 14 and the third pneumatic valve 15 are closed, and the second pumping is carried out on the carbon dioxide laser ultra-high vacuum sample melting system 29 by the first molecular pump 5 for the high vacuum state. When the reading of the first ionization gauge 12 is as low as (~$10^{-5}$ Pa), the method of baking the meteorite sample described by Wang Ying et al. in 2018 (Method of determining noble gases in trace meteorite specimens using a laser microprobe, Acta Petrologica Sinica) is adopted to remove the adsorbed gas at a baking temperature of 120° C. After baking, when the lunar soil sample is cooled to room temperature of 20° C., the ninth pneumatic valve 31 and the first pneumatic valve 13 are closed, the eighth pneumatic valve 28 and the tenth pneumatic valve 35 are opened, and the ultra-high vacuum state of the carbon dioxide laser ultra-high vacuum sample melting system 29 is realized by the sputtering ion pump 36 through the second zirconium-aluminum getter 33 and the third CF four-way 34.

3) Extraction and purification: the extraction method of noble gases in lunar soil samples is described by Wang Ying et al. in 2018 (Method of determining noble gases in trace meteorite specimens using a laser microprobe, Acta Petrologica Sinica). Due to the distinct nature of the lunar soil sample compared to Earth samples, characterized by its minimal content of water and hydrocarbons (CxHx), it is feasible to directly directly purify the gas by zirconium-aluminum getter to remove active gases such as hydrogen and nitrogen, and finally only noble gases remain. In this scheme, the fifth pneumatic valve 19, the seventh pneumatic valve 24, the tenth pneumatic valve 35, the eleventh pneumatic valve 37 and the twelfth pneumatic valve 40 are closed, and the sixth pneumatic valve 22 and the eighth pneumatic valve 28 are opened, so that the first zirconium-aluminum getter 21 and the second zirconium-aluminum getter 33 can efficiently purify the extracted lunar soil gas, and the active gas in the extraction gas is removed, leaving only the extracted noble gas.

4) Diffusion of noble gas: after purification, the noble gas extracted from lunar soil is diffused into an enclosed diffusion area (volume V1). The enclosed diffusion area is formed by closing the third pneumatic valve 15, the fourth pneumatic valve 17, the seventh pneumatic valve 24, the tenth pneumatic valve 35, the eleventh pneumatic valve 37, the thirteenth pneumatic valve 42, the fifteenth pneumatic valve 46 and the sixteenth pneumatic valve 47, opening the fifth pneumatic valve 19, the sixth pneumatic valve 22, the twelfth pneumatic valve 40 and the fourteenth pneumatic valve 44, and connecting the first CF tee 16, the first CF two-way 20, the first zirconium-aluminum getter 21, the second CF cross 23, the third CF cross 34, the fifth CF cross 41 and the dilution tank 45 of the gas pipeline. After diffusion, by closing the fifth pneumatic valve 19, the gas in the enclosed diffusion area is divided into two groups (volumes V2 and V3), the first group is located in the first enclosed diffusion area (V2) of the first CF tee 16, and the second group is located in the remaining second enclosed diffusion area (V3).

5) Gas capture: as for gas in an enclosing area formed by closing the fifth pneumatic valve 19, the seventh pneumatic valve 24, the tenth pneumatic valve 35, the eleventh pneumatic valve 37, the thirteenth pneumatic valve 42, the fifteenth pneumatic valve 46 and the sixteenth pneumatic valve 47, opening the sixth pneumatic valve 22, the twelfth pneumatic valve 40 and the fourteenth pneumatic valve 44, and connecting the first CF tee 16, the first CF two-way 20, the first zirconium-aluminum getter 21, the second CF cross 23, the third CF cross 34, the fifth CF cross 41 and the dilution tank 45 of the gas pipeline, it is necessary to open the thirteenth pneumatic valve 42, and the argon, krypton and xenon gases in the enclosed area could be captured by using the cryopump 43 (volume V4) without activated carbon and setting the temperature at 60K. After the capture is completed, the eleventh pneumatic valve 37 and the fifteenth pneumatic valve 46 are opened, and the helium and neon gas not being captured in the enclosed area in the pipeline are pumped by the second molecular pump 9. When the reading of the second ionization gauge 39 shows (~$10^{-7}$ Pa), the eleventh pneumatic valve 37, the thirteenth pneumatic valve 42, the fourteenth pneumatic valve 44 and the fifteenth pneumatic valve 46 are closed. The seventh pneumatic valve 24 and the tenth pneumatic valve 35 are opened, and the enclosed area is pumped by the sputtering ion pump 36 until the pipelines are restored to the ultra-high vacuum state. The gas exists in the closed area composed of controlling the third pneumatic valve 15, the fourth pneumatic valve 17 and the fifth pneumatic valve 19, the tenth pneumatic valve 35 in the pipelines is closed to isolate the pumping of the sputtering ion pump 36, and the fifth pneumatic valve 19 is opened, so that the activated carbon-containing cold trap 25 comes into contact with the gas. By controlling the liquid nitrogen support 26, the activated carbon cold trap 25 is immersed in liquid nitrogen, and the argon in the gas is captured at the temperature of 77K. After the capture is completed, the seventh pneumatic valve 24 is closed. The fourth pneumatic valve 17 is opened to realize the communication between the cryopump 18 containing activated carbon and the gas, and the temperature is set at 35K to realize the capture of neon in the gas. After the capture is completed, theoretically, the gas in the pipelines only consists of helium.

6) Gas measurement: the overall process sequence is to measure helium-neon-argon (the first time)-argon (the second time)-krypton-xenon successively. The specific steps of helium-neon-argon (the first time) are as follows: the fourth pneumatic valve 17 and the twelfth pneumatic valve 40 are closed, and only the helium gas in the fifth CF four-way 41 in the enclosed area is taken, the sixteenth pneumatic valve 47 is opened, and the helium gas in the fifth CF four-way 41 in the enclosed area enters the noble gas mass spectrometer 48 (the volume is VMS) for measurement; after gas intake, and the sixteenth pneumatic valve 47 is closed; the third pneumatic valve 15 is opened, and the remaining helium in the pipelines is pumped by the first molecular pump 5, and when the reading of the first ionization gauge 12 is ~$10^{-7}$ Pa, the third pneumatic valve 15 is closed, and the tenth pneumatic valve 35 is opened, the sputtering ion pump 36 is used for pumping until the pipelines are restored to the ultra-high vacuum state. After pumping, the tenth pneumatic valve 35 in the pipelines is closed to isolate the sputtering ion pump 36, and the fourth pneumatic valve 17 is opened, the cryopump 18 containing activated carbon is set to a temperature of 80K, and the neon gas is released into the pipelines. After release, the flow consistent with helium gas intake is repeated to measure neon gas, and then the operation flow consistent with helium gas pumping in the pipelines is repeated to restore the pipelines to the ultra-high vacuum state. After the pumping, the tenth pneumatic valve 35 in the pipelines is closed, and the seventh pneumatic valve 24 is opened to control the liquid nitrogen support 26 to remove liquid nitrogen, and then the temperature-controlled heating wire 27 heats the cold trap 18 containing activated carbon at a heating temperature of 370K, releasing argon gas into the pipelines. After the release, the sixteenth pneumatic valve 47 is closed (the volume of the fifth CF cross 41 in the enclosed area is characterized as V5), and the measuring flow consistent with helium and neon gas is repeated to measure the argon gas (for the first time). Then, the operation flow consistent with helium and neon gas pumping in the pipelines is repeated, additionally, the seventh pneumatic valve 24 is closed to ensure that the pipelines are returned to the ultra-high vacuum state.

The specific measurement steps of argon (the second time)-krypton-xenon are as follows: after pumping, the tenth pneumatic valve 35 in the pipelines is closed, the twelfth pneumatic valve 40 in the pipelines is closed, the thirteenth pneumatic valve 42 is opened, the cryopump 43 without activated carbon is set at a temperature of 80K, and the argon gas is released into the pipelines (the volume of the third enclosed diffusion area is V6, and the third enclosed diffusion area includes the fifth CF four-way 41 and the cryopump 43 without activated carbon); after release, the intake procedure consistent with that of the first measurement of argon gas is repeated to measure the argon gas (for the second time); after gas intake, the operation flow consistent with argon pumping (for the first time) is repeated and the seventh pneumatic valve 24 is additionally closed to restore the pipelines to the ultra-high vacuum state; after pumping, the twelfth pneumatic valve 40 in the pipelines is closed, the thirteenth pneumatic valve 42 is opened, the cryopump 43 without activated carbon is set at a temperature of 103K, and the krypton gas is release into the pipelines; after release, the sixteenth pneumatic valve 47 is opened, and the krypton gas enters the noble gas mass spectrometer 48 for krypton gas measurement, after gas intake, the sixteenth pneumatic valve 47 is closed; the twelfth pneumatic valve 40 in the pipelines is opened, and the pipelines are pumped by the sputtering ion pump 36 to restore the pipelines to the ultra-high vacuum state. The above krypton gas intake measurement steps are repeated, and only the cryopump 43 without activated carbon is set at a temperature of 155K, and the xenon gas is released; after gas intake measurement, the twelfth pneumatic valve 40 in the pipelines is opened, and the sputtering ion pump 36 pumps to restore the pipelines to the ultra-high vacuum state.

The above-mentioned embodiments only illustrate the principle and efficacy of the present disclosure, and are not used to limit the present disclosure. Anyone familiar with this technology can modify or change the above embodiments without violating the spirit and scope of the present disclosure. Therefore, all equivalent modifications or changes made by people with ordinary knowledge in the technical field without departing from the spirit and technical ideas disclosed in the present disclosure should still be covered by the claims of the present disclosure.

What is claimed is:

1. A test device for isotope measurement of noble gases in lunar soil, comprising a carbon dioxide laser ultra-high vacuum sample melting system (29), a first zirconium-aluminum getter (21), a second zirconium-aluminum getter (33), a vacuum dry pump (1), a first molecular pump (5), a second molecular pump (9), a neon gas capture unit, an argon gas capture unit, an argon-krypton-xenon capture unit, a dilution tank (45), a sputtering ion pump (36) and a noble gas mass spectrometer (48) which are connected through pipelines;

the pipelines comprise a first CF cross (11), a first CF tee (16), a first CF two-way (20), a second CF cross (23), a second CF two-way (30), a second CF tee (32), a third CF cross (34), a fourth CF cross (38) and a fifth CF cross (41), wherein four ports of the first CF cross (11) are respectively connected with the first molecular pump (5), the second CF tee (32), the first CF tee (16) and the pressure detection unit; the remaining two ports of the second CF tee (32) are respectively connected with the second CF two-way (30) and the vacuum dry pump (1); the other port of the second CF two-way (30) is connected with the carbon dioxide laser ultra-high vacuum sample melting system (29);

the remaining two ports of the first CF tee (16) are respectively connected with the neon gas capture unit and the first zirconium-aluminum getter (21) through the first CF two-way (20);

the four ports of the second CF cross (23) are respectively connected with the first zirconium-aluminum getter (21), the argon gas capture unit, the second zirconium-aluminum getter (33) and the carbon dioxide laser ultra-high vacuum sample melting system (29);

the four ports of the third CF cross (34) are respectively connected with the second zirconium-aluminum getter (33), the sputtering ion pump (36), the fourth CF cross (38) and the fifth CF cross (41);

the remaining three ports of the fourth CF cross (38) are respectively connected with a pressure detection unit, the dilution tank (45) and the second molecular pump (9);

the remaining three ports of the fifth CF cross (41) are respectively connected with the argon-krypton-xenon capture unit, the dilution tank (45) and the noble gas mass spectrometer (48);

and control valves for controlling opening and closing of the pipelines are installed on a connection path between each pipeline and each component.

2. The testing device according to claim 1, wherein the control valves are all pneumatic valves.

3. The testing device according to claim 2, wherein the second CF tee (32) connects to the first CF cross (11) via a first pneumatic valve (13) and to the vacuum dry pump (1) via a second pneumatic valve (14);

the first CF tee (16) connects to the first CF cross (11) via a third pneumatic valve (15), to the neon gas capture unit via a fourth pneumatic valve (17) and to the first CF two-way (20) via a fifth pneumatic valve (19);

the second CF cross (23) connects to the first zirconium-aluminum getter (21) via a sixth pneumatic valve (22), to the argon gas capture unit via a seventh pneumatic valve (24) and to the carbon dioxide laser ultra-high vacuum sample melting system (29) via an eighth pneumatic valve (28);

the second CF two-way (30) connects to the second CF tee (32) via a ninth pneumatic valve (31);

the third CF cross (34) connects to the sputtering ion pump (36) via a tenth pneumatic valve (35), to the fourth CF cross (38) via an eleventh pneumatic valve (37) and to the fifth CF cross (41) via a twelfth pneumatic valve (40);

the fifth CF cross (41) connects to the argon-krypton-xenon capture unit via a thirteenth pneumatic valve (42), to the dilution tank (45) via a fourteenth pneumatic valve (44) and to the noble gas mass spectrometer (48) via a sixteenth pneumatic valve (47).

4. The testing device according to claim 1, wherein the neon gas capture unit is a cryopump (18) containing activated carbon; and/or the argon-krypton-xenon capture unit is a cryopump (43) without active carbon.

5. The testing device according to claim 1, wherein an oxygen-free copper gasket is positioned at a sample cavity entrance of the carbon dioxide laser ultra-high vacuum sample melting system (29) for sealing a sample cavity.

6. The testing device according to claim 1, wherein the argon gas capture unit comprises an activated carbon-containing cold trap (25), a liquid nitrogen bracket (26) and a temperature-controlled heating wire (27), wherein the activated carbon-containing cold trap (25) is arranged in the liquid nitrogen bracket (26), and the temperature-controlled heating wire (27) is arranged outside the activated carbon-containing cold trap (25), and the activated carbon-containing cold trap (25) is used for communicating with the second CF cross (23).

7. The testing device according to claim 1, wherein the device further comprises a first bellows (2), a second bellows (4), a third bellows (8), a first isolation valve (3), a KF tee (6) and a second isolation valve (7);

the first molecular pump (5) is sequentially connected with the second bellows (4), the first isolation valve (3) and the first bellows (2), and then connected with the vacuum dry pump (1);

the second molecular pump (9) is sequentially connected with the third bellows (8), the second isolation valve (7) and the KF tee (6), and then connected with the pressure detection unit and the vacuum dry pump (1) respectively;

the remain port of the KF tee (6) is connected with the pressure detection unit.

8. The test device according to claim 1, wherein the pressure detection unit is selected from a resistance gauge or an ionization gauge; and/or the first zirconium-aluminum getter (21) and the second zirconium-aluminum getter (33) respectively comprise at least one zirconium-aluminum pump; and/or volumes of the pipelines and components of the test device are known constants.

9. A test method for isotope measurement of noble gases in lunar soil, applying the test device according to claim 1, comprising the following steps:

1) loading of the lunar soil sample:

keeping the test device under vacuum conditions except the carbon dioxide laser ultra-high vacuum sample melting system (29) by manipulating the control valve, and loading the lunar soil sample into the cavity of the carbon dioxide laser ultra-high vacuum sample melting system (29);

2) removal of adsorbed gas from the lunar soil sample surface:

2-1) only maintaining the carbon dioxide laser ultra-high vacuum sample melting system (29), the second CF two-way (30) and the second CF tee (32) in conjunction with the vacuum dry pump (1) to establish a conduction transport pathway by manipulating the control valve, so as to carry out the first pumping on the carbon dioxide laser ultra-high vacuum sample melting system (29) by the vacuum dry pump (1);

2-2) baking the lunar soil sample; only maintaining the carbon dioxide laser ultra-high vacuum sample melting system (29), the second CF two-way (30) and the second CF tee (32) in conjunction with the first molecular pump (5) to establish a conduction transport pathway by manipulating the control valve, so as to carry out the second pumping on the carbon dioxide laser ultra-high vacuum sample melting system (29) by the first molecular pump (5);

2-3) terminating the baking process, and when the lunar soil sample is cooled to room temperature, only maintaining the carbon dioxide laser ultra-high vacuum sample melting system (29), the second zirconium-aluminum getter (33) and the third CF cross (34) in conjunction with the sputtering ion pump (36) to establish a conduction transport pathway by manipulating the control valve, so as to carry out the third pumping on the carbon dioxide laser ultra-high vacuum sample melting system (29) by the sputtering ion pump (36);

3) extraction and purification:
3-1) heating the lunar soil sample through the diamond window by the carbon oxide laser for gas extraction to obtain extracted lunar soil gas;
3-2) only maintaining the first zirconium-aluminum getter (21) and the second zirconium-aluminum getter (33) in conjunction with the carbon dioxide laser ultra-high vacuum sample melting system (29) to establish a conduction transport pathway by manipulating the control valve, enabling the first zirconium-aluminum getter (21) and the second zirconium-aluminum getter (33) to purify the extracted lunar soil gas;

4) diffusion of noble gas:
4-1) diffusing the noble gas extracted from lunar soil by manipulating the control valve to an enclosed diffusion area, the enclosed diffusion area is formed by the first CF tee (16), the first CF two-way (20), the first zirconium-aluminum getter (21), the second CF cross (23), the third CF cross (34), the fifth CF cross (41) and the dilution tank (45);
4-2) dispersing the noble gas in the enclosed diffusion area into a first enclosed diffusion area and a second enclosed diffusion area by manipulating the opening and closing of the control valve between the first CF tee (16) and the first CF two-way (20), wherein the first enclosed diffusion area is in the first CF tee (16) and the second enclosed diffusion area is the enclosed diffusion area except the first enclosed diffusion area;

5) gas capture:
5-1) by manipulating the control valve and by closing the control valve between the first CF tee (16) and the first CF two-way (20), only maintaining the first CF two-way (20), the first zirconium-aluminum getter (21), the second CF cross (23), the third CF cross (34), the fifth CF cross (41) and the dilution tank (45) in conjunction with the argon-krypton-xenon capture unit to establish a conduction transport pathway, capturing argon, krypton and xenon gases in the noble gases in the second enclosed diffusion area by the argon-krypton-xenon capture unit to obtain argon-krypton-xenon gas; and carrying out the fourth pumping on the helium gas and neon gas not being captured in the pipelines by the second molecular pump (9) by manipulating the control valve after capture;
5-2) by opening the control valve between the first CF tee (16) and the first CF two-way (20), only maintaining the argon gas capture unit communicating with the noble gases in the first enclosed diffusion area, enabling the argon gas capture unit to capture argon gas in the noble gases;
5-3) only maintaining the neon gas capture unit communicating with the noble gases in the first enclosed diffusion area by manipulating the control valve, enabling the neon gas capture unit to capture the neon gas in the first enclosed diffusion area;

6) gas measurement:
specific measurement steps of helium, neon, and argon for the first time are as follows:
6-1) only enabling helium gas in the fifth CF cross (41) in the enclosed area into the noble gas mass spectrometer (48) by manipulating the control valve for measurement, and pumping the remaining helium gas in the pipelines by the first molecular pump (5) to remove the helium gas in the pipelines after measurement;
6-2) releasing the neon gas in the neon gas capture unit into the pipelines by manipulating the control valve, enabling the neon gas to enter the noble gas mass spectrometer (48), and pumping the remaining neon gas in the pipelines by the first molecular pump (5) to remove the neon gas in the pipelines after measurement;
6-3) releasing the argon gas in the argon gas capture unit into the pipelines by manipulating the control valve, opening the sixteenth pneumatic valve (47) after release to make the argon enter the noble gas mass spectrometer (48), and pumping the remaining argon gas in the pipelines by the first molecular pump (5) to remove the argon gas in the pipelines after measurement;
specific measurement steps of argon (for the second time), krypton and xenon are as follows,
6-4) wherein the argon-krypton-xenon capture unit is a cryopump (43) without activated carbon; setting the cryopump (43) without activated carbon at a temperature of 78-82 K, and releasing the argon into the third enclosed diffusion area, the third enclosed diffusion area comprises the fifth CF cross (41) and the cryopump (43) without activated carbon; opening the sixteenth pneumatic valve (47) to make the argon gas enter the noble gas mass spectrometer (48), and pumping the remaining argon gas in the pipelines by the first molecular pump (5) to remove the argon gas in the pipelines after measurement;
6-5) setting the cryopump (43) without activated carbon at a temperature of 101-105 K, releasing krypton gas into the third enclosed diffusion area to make the krypton gas enter the noble gas mass spectrometer (48), and pumping the remaining krypton gas in the pipelines by the first molecular pump (5) to remove the krypton gas in the pipelines after measurement;
6-6) setting the cryopump (43) without activated carbon at a temperature of 152-157 K, releasing xenon gas into the third enclosed diffusion area to make the xenon gas enter the noble gas mass spectrometer (48); and pumping the remaining xenon gas in the pipelines with the first molecular pump (5) to remove the xenon gas in the pipelines after measurement.

10. The test method according to claim 9, wherein the first isolation valve (3) and the second isolation valve (7) are closed during the first pumping;
and/or, the first pumping is at an end point of 0.1-10 Pa;
and/or, the second pumping is at an end point of $0.5-2*10^{-5}$ Pa;
and/or, the third pumping is at an end point of $(0.5-2)*10^{-8}$ Pa; and/or, the fourth pumping is at an end point of $0.5-2*10^{-7}$ Pa and/or the fifth pumping is at an end point of $0.5-2*10^{-7}$ Pa.

* * * * *